(12) United States Patent
Decitre

(10) Patent No.: US 8,159,217 B2
(45) Date of Patent: Apr. 17, 2012

(54) METHOD AND DEVICE WITH SEPARATE EMISSION/RECEPTION FUNCTIONS FOR MAKING EDDY CURRENT TESTS ON AN ELECTRICALLY CONDUCTING PART

(75) Inventor: Jean-Marc Decitre, Marcoussis (FR)

(73) Assignee: Commissariat a l'Energie Atomique, Paris (FR)

( * ) Notice: Subject to any disclaimer, the term of this patent is extended or adjusted under 35 U.S.C. 154(b) by 320 days.

(21) Appl. No.: 12/376,112

(22) PCT Filed: Jul. 30, 2007

(86) PCT No.: PCT/EP2007/057851
§ 371 (c)(1),
(2), (4) Date: Dec. 3, 2009

(87) PCT Pub. No.: WO2008/015197
PCT Pub. Date: Feb. 7, 2008

(65) Prior Publication Data
US 2010/0134100 A1    Jun. 3, 2010

(30) Foreign Application Priority Data
Aug. 3, 2006   (FR) ...................... 06 53277

(51) Int. Cl.
*G01N 27/82*    (2006.01)

(52) U.S. Cl. ...................................... 324/241

(58) Field of Classification Search .................. None
See application file for complete search history.

(56) References Cited

U.S. PATENT DOCUMENTS

| | | | | |
|---|---|---|---|---|
| 3,875,502 A | * | 4/1975 | Neumaier | 324/241 |
| 4,107,605 A | * | 8/1978 | Hudgell | 324/220 |
| 5,047,719 A | * | 9/1991 | Johnson et al. | 324/242 |
| 5,302,895 A | * | 4/1994 | Philpot | 324/220 |
| 5,506,503 A | * | 4/1996 | Cecco et al. | 324/220 |
| 5,659,248 A | | 8/1997 | Hedengren et al. | |
| 6,310,476 B1 | | 10/2001 | Kawanami et al. | |
| 6,501,267 B1 | * | 12/2002 | Kurokawa et al. | 324/242 |

FOREIGN PATENT DOCUMENTS

| | | |
|---|---|---|
| EP | 0061956 A1 | 10/1982 |
| EP | 0177626 A1 | 4/1986 |
| FR | 2260113 A1 | 8/1975 |
| FR | 2773397 A1 | 7/1999 |
| FR | 2881826 A1 | 8/2006 |

OTHER PUBLICATIONS

International Search Report, PCT/EP2007/057851, dated Nov. 6, 2007.

* cited by examiner

*Primary Examiner* — Paresh Patel
(74) *Attorney, Agent, or Firm* — Nixon Peabody LLP

(57) ABSTRACT

A method for making eddy current tests on an electrically conducting part (13), in which a sensor moves above this part, uses separate emission/reception functions. The method includes obtaining a first complex voltage curve at the terminals of a reception winding (12), obtaining at least one second complex voltage curve at the terminals of a reception winding, determining at least one given distance that minimizes the modulus of the difference between the first curve and the at least one second curve, calculating the arithmetic mean (d) of the at least one given distance, choosing this arithmetic mean+/−20% as the distance between the two emission and reception windings, and detecting if one or several defects are present in this part.

12 Claims, 2 Drawing Sheets

METHOD AND DEVICE WITH SEPARATE EMISSION/RECEPTION FUNCTIONS FOR MAKING EDDY CURRENT TESTS ON AN ELECTRICALLY CONDUCTING PART

CROSS REFERENCE TO RELATED APPLICATIONS OR PRIORITY CLAIM

This application is a national phase of International Application No. PCT/EP2007/057851, entitled "METHOD AND DEVICE FOR CHECKING USING EDDY CURRENTS WITH SEPARATE EMISSION/RECEPTION FUNCTIONS AN ELECTRICALLY CONDUCTING PART TESTS ON AN ELECTRICALLY CONDUCTING PART", which was filed on Jul. 30, 2007, and which claims priority of French Patent Application No. 06 53277, filed Aug. 3, 2006.

DESCRIPTION

1. Technical Field

The invention relates to a method and a device with separate emission/reception functions for making eddy current tests on an electrically conducting part.

2. State of Prior Art

The field of the invention is eddy current tests on an electrically conducting part with separate emission/reception functions, with a wide operating range using a very compact set of emission and reception windings. Such a test is particularly advantageous for the detection of small defects, particularly for non-destructive testing (NDT) of electrically conducting parts.

The principle of using eddy currents to detect defects in an electrically conducting part consists of using an emission winding to emit an electromagnetic field at a frequency adapted to the conductivity of the material and the depth of the defects being searched for, close to this part. The next step is to measure an electromotive force at the terminals of at least one reception winding, generated by direct coupling of magnetic field lines between the emission winding and the reception winding in the presence of the conducting part. A small variation in this electromotive force that is superposed on it when a defect is present in the material is also measured. The field of the invention is thus restricted to methods and devices using at least one winding assigned to emission of the electromagnetic signal capable of generating eddy currents in the part to be tested, and at least one winding assigned to reception of signals induced by the eddy currents, such a configuration being said to have "separate functions".

The induced electromotive force $V_R$ at the terminals of each reception winding, that is at the same frequency as the current sent into the associated emission winding, is used to obtain the useful signal after demodulation. In the presence of a defect, this induced electromotive force $V_R$ becomes $V_R \pm \delta V_R$, and only the variation $\delta V_R$ that is very small compared with $V_R$, carries information.

Detection of defects, and particularly small defects, makes it necessary to use small windings (small elements), and therefore detected signals have very low amplitudes. Devices according to prior art have combinations of several windings to solve such problems.

Thus, document reference [1] at the end of the description describes an eddy current device for detection of defects comprising at least one detection probe composed of one emission winding and four detection windings to detect the magnetic field induced in the part to be tested. The reception windings are arranged such that their centres form the vertices of a diamond, forming a first and second pair of windings, the first pair arranged on one diagonal of this diamond being connected in common mode, the second pair arranged on the other diagonal being connected in common mode, this first and second pairs of reception windings being connected in differential mode. The emission winding into which an alternating current is input, is arranged above these reception windings, the centre of the reception winding being arranged above the centre of the diamond. The device also includes a device for switching operation of each of these probes. Thus, for each probe, this device comprises several reception windings arranged symmetrically about an emission winding and connected differentially.

This defect detection device has several disadvantages, particularly its weight, its cost, and also defects inherent to differential assemblies: undesirable signals are only eliminated if they appear at the same time on two windings connected in opposition with the same amplitude and the same phase. Furthermore, associated windings and their corresponding measurement channels must have identical characteristics.

Furthermore, in this document reference [1], when the defect detection device moves above the part to be tested, variations in the air gap, in other words variations in height between this device and this part, can disturb the useful signal. These air gap variations are mainly due to:

vibrations during displacement of the device, and the fact that the device cannot precisely match the local surface of a complex part.

The purpose of the invention is to correct such disadvantages by proposing a method and a device with separate emission/reception functions for making eddy current tests on an electrically conducting part, that is not very sensitive to air gap noise minimising the variation of the useful signal due to an accidental air gap variation.

PRESENTATION OF THE INVENTION

The invention relates to a method with separate emission/reception functions for making eddy current tests on an electrically conducting part with an electrical conductivity $\sigma_1$ and relative magnetic permeability $\mu_{r1}$, in which a sensor comprising at least one assembly formed from at least one emission winding emitting an electromagnetic field and at least one reception winding influenced by the electromagnetic fields produced by eddy currents induced in this part, moves above this part, characterised in that it comprises the following steps:

obtain a first complex voltage curve at the terminals of a reception winding, depending on the distance between the corresponding emission winding and this reception winding, for the nominal distance between the sensor and a portion of this part without any defects or another part without any defects, for example for which the electrical conductivity $\sigma_2$ is such that $0.05 \times \sigma_1 \leq \sigma_2 \leq 20 \times \sigma_1$ and the relative magnetic permeability $\mu_{r2}$ is such that $0.05 \times \mu_{r1} \leq \mu_{r2} \leq 20 \times \mu_{r1}$, obtain at least one second complex voltage curve at the terminals of a reception winding, as a function of the distance between the corresponding emission winding and this reception winding, for at least one distance (e) different from the nominal distance between the sensor and a portion of this part with no defects or another part without any defects, determine at least one given distance that minimises the modulus of the difference between the first curve and the at least one second curve, calculate the arithmetic mean of the at least one given distance, choose this arithmetic mean+/−20% as the distance between the two emission and reception windings detect if one or several defects are present in this part.

Advantageously, the emission and reception windings are arranged on each side of a support that may be flexible, for example a kapton film, in which the windings are etched. Advantageously, the frequency range used is between a few Hertz, for example 10 Hertz, and 50 MHz.

Advantageously, a magnetic material is placed at the centre of each winding and/or close to each winding, on the side opposite the part to be tested, so as to reduce the reluctance of the magnetic circuit in each emission winding/reception winding pair.

The method according to the invention has the following advantages in particular:

It optimises the distance between the emission winding and the reception winding of the sensor so as to minimise the influence of the air gap noise on the useful signal.

A single sensor can be adapted to different parts to be tested with several radii of curvature, by scanning surfaces with three dimensions with a fine spatial resolution.

If the support wear surface, for example a kapton film, becomes thinner during repeated scans of the sensor on the part to be tested, the settings of the instrument containing the sensor (particularly balancing) remain identical.

A sensor on a kapton film enables simultaneous etching of emission and reception windings, their power supply wires and their connectors, which reduces production and maintenance costs due to the lack of soldering.

The sensor thus obtained has good sensitivity, a good signal-to-noise ratio, and enables a high winding density due to overlap of the emission and reception windings.

The method according to the invention can be used in many domains, and particularly:

in the nuclear domain for swaging transition zones (ZTD) in steam generator tubes, in the aeronautical field, for complex parts.

The invention also relates to a device with separate emission/reception functions for making eddy current tests on an electrically conducting part, characterised in that it comprises:

at least two rows, for example at different heights, composed of at least one element formed from at least one emission winding emitting an electromagnetic field and at least one reception winding, for example arranged on each side of a support, and in that:

each row is offset from the next row by a distance p, each winding of the same nature on a particular row being at a distance n×p from its closest neighbour, where n is the number of rows.

the distance between an emission winding and a reception winding of each element in each of the rows is equal to d+/−20%, where d is the calculated arithmetic mean of at least one distance (di) that minimises the modulus of the difference between a complex voltage curve for a nominal distance between the sensor and a portion of this part without any defects or another part without any defects, and at least one complex voltage curve for distance different from the nominal distance.

Advantageously, electrical insulation is placed between two consecutive rows.

DETAILED PRESENTATION OF PARTICULAR EMBODIMENTS

Figure 1:
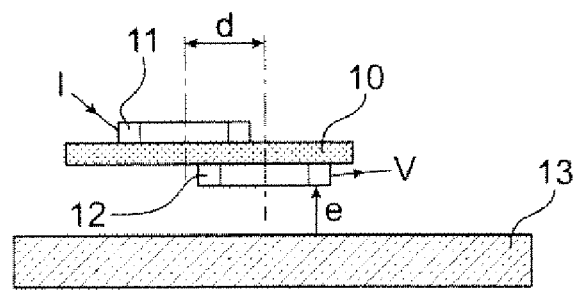
FIG. 1 shows a principle diagram for a sensor implementing the method according to the invention.

The sensor showed in FIG. 1 comprises an emission winding 11 (radius r1) and a reception winding 12 (radius r2) placed on each side of a support 10. These windings 11 and 12 may for example be etched on each side of a kapton flexible support 10. A current I passes through the winding 11 that is arbitrarily chosen as the emission winding. The winding 12 is then the reception winding, at the terminals of which a voltage V is measured.

These two windings 11 and 12 may advantageously have the same geometric characteristics. Their centres are separated by a distance d. All of these windings 11 and 12 on the support 10 are located at a distance e, called the air gap, from a conducting part 13 to be tested.

In the absence of a defect in the part 13, the voltage V measured at the terminals of the reception winding 12 is due to electromagnetic coupling between the two windings 11 and 12: a part of the alternating magnetic field emitted by the emission winding 11 passes through the reception winding 12. This magnetic field induces a voltage of the same frequency that is called the coupling voltage or mutual induction.

Figure 2:
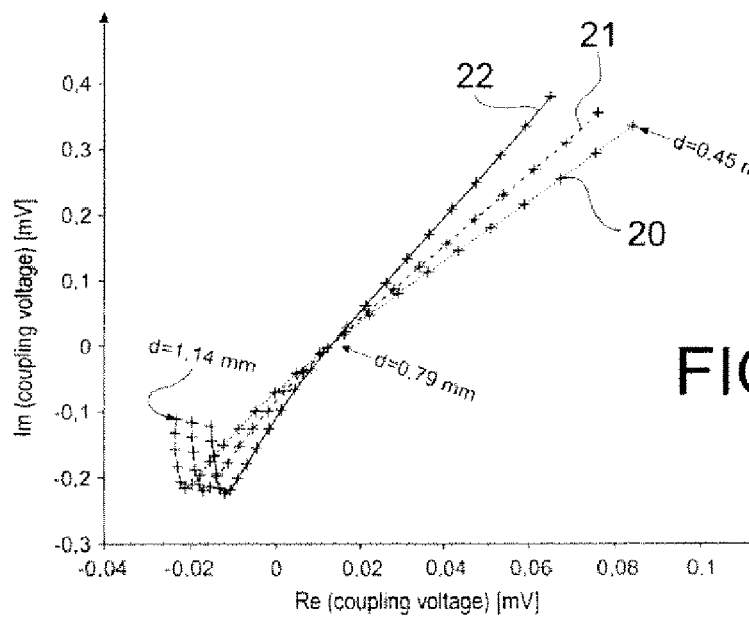
FIG. 2 shows the complex coupling voltage obtained at the terminals of a reception winding of a sensor as a function of the distance d between the corresponding emission winding and this reception winding.

FIG. 2 shows the complex coupling voltage obtained at the terminals of the reception winding 12 as a function of the distance d (in mm) between the two windings 11 and 12 for three air gap values:

e=100 μm: curve 20, e=120 μm: curve 21, and e=150 μm: curve 22.

The other parameters are as follows:

outside diameter of windings 11 and 12: 1 mm, inside diameter of windings 11 and 12: 0.5 mm, each winding 11 and 12 being formed from six turns with a pitch of 45 μm and a height of 5 μm, a 50 μm thick flexible support 10, working frequency: 10 MHz.

The method according to the invention includes the following steps:

obtain a first complex voltage curve 20 at the terminals of a reception winding 12, as a function of the distance between the corresponding emission winding 11 and this reception winding, for the nominal distance that is equal to the average distance between the part and the closest portion of the windings when the sensor is in contact on the part (minimum air gap value), between the sensor and a portion of this part without any defects or another part without any defects, for example the electrical conductivity $\sigma_2$ is such that $0.05 \times \sigma_1 \leq \sigma_2 \leq 20 \times \sigma_1$ and the relative magnetic permeability $\mu_{r2}$ is such that $0.05 \times \mu_{r1} \leq \mu_{r2} \leq 20 \times \mu_{r1}$, obtain at least one second complex voltage curve 21, 22 at the terminals of a reception winding, as a function of the distance between the corresponding emission winding and this reception winding, for at least one distance e different from the nominal distance between the sensor and a portion of this part without any defects or another part without any defects, determine at least one given distance di that minimises the modulus of the difference between the first curve 20 and the at least one second curve 21, 22, calculate the arithmetic mean d of the at least one given distance di, this arithmetic mean d being equal to the value of di when there is only a distance di, choose this arithmetic mean+/−20% as the distance between the two emission and reception windings detect the presence of one or several defects in this part.

Figure 3:
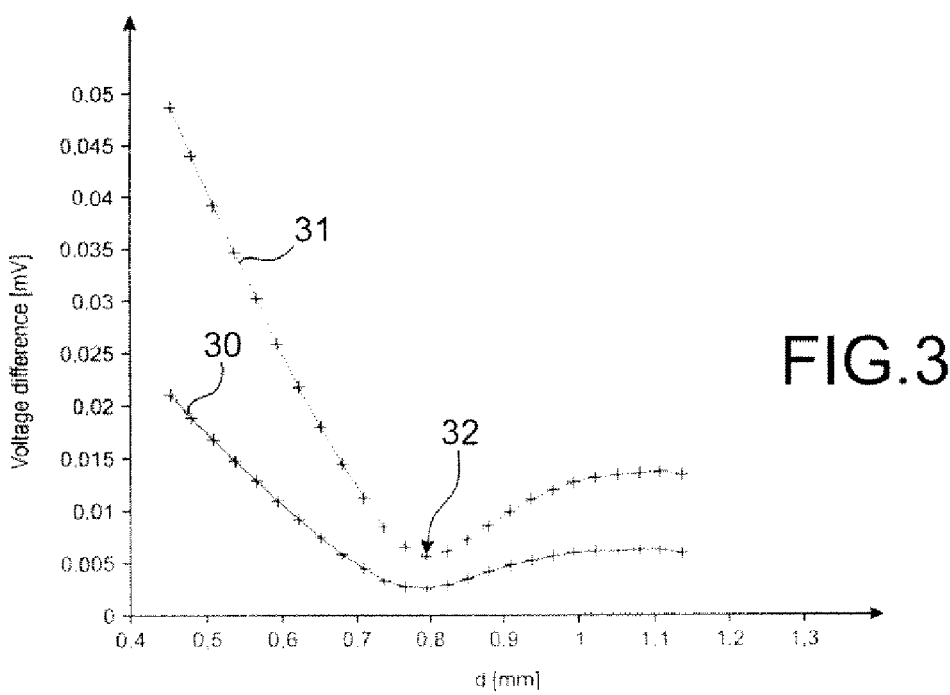
FIG. 3 shows the coupling voltage differences between the curves in FIG. 2.

Differences in the coupling voltage between curves 21 and 22 and the reference curve 20 are shown on curves 30 and 31 in FIG. 3.

It can be seen that these curves 30 and 31 pass through a minimum 32 for abscissas d1=790 μm and d2=788 μm for the two air gap jumps of 20 μm and 50 μm. Therefore these distances d1 and d2 minimise the influence of a variation in the air gap. Therefore, the method according to the invention includes an arrangement of the windings 11 and 12 at a distance d=(d1+d2)/2±20%.

Figure 4:
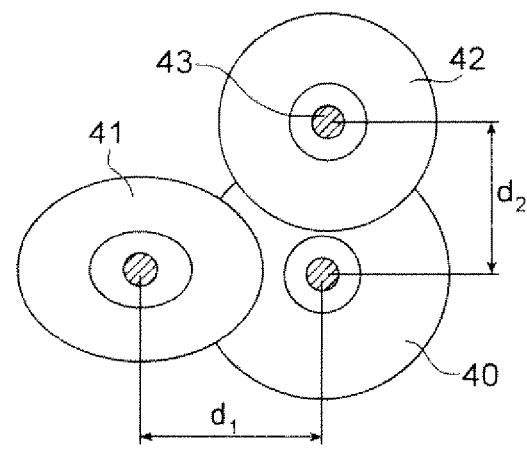
FIG. 4 shows an example embodiment of an optimised sensor obtained using the process according to the invention.

One example embodiment of a sensor optimised in this way and that is therefore less noisy particularly on complex surfaces, is illustrated as shown in FIG. 4. In this example, there is an overlap between the emission winding 40 and each reception winding 41 and 42. Each optimised distance d1 (between windings 40 and 41) and d2 (between windings 40 and 42) is greater than the smallest of the radii of windings 40, 41 or 42 and less than the sum of the radii of the two corresponding emission and reception windings. In this example, each winding comprises a metallised hole 43 at its centre. But, the emission and/or reception windings can only have a single turn. In this case, the metallised holes 43 are not necessary.

The optimum distance d between the emission winding and a reception winding 41 or 42 can be found experimentally:

by etching the emission winding 40 and a reception winding 41 and 42 on two distinct supports and measuring the coupling voltage for different values d and e, or by testing a series of elements, each with an emission winding 40 and one or several reception windings 41, 42 with variable distances d between the emission and reception windings.

The method according to the invention is advantageously used within a range of frequencies normally used in the field of non-destructive testing using eddy currents, in other words a few Hertz, for example 10 Hertz, to 50 MHz.

A sensor comprising the following may be used in various embodiments of the method according to the invention:

emission and reception windings with different geometric characteristics, several non-identical reception windings placed at distances d from an emission winding, optimised by the method according to the invention, complex shaped emission and reception windings, for example arbitrary polygonal or oval turn(s), emission and reception windings of an element composed of several windings connected in series. For example, a winding may be composed of two coaxial windings etched facing each other on each face of a kapton film and connected in series through the metallised hole, and for which the winding directions are such that the voltages at their terminals are additive, emission or reception windings composed of two (or more) non-coaxial windings connected differentially and at a distance from the corresponding emission winding equal to one near-distance.

a magnetic material arranged at the centre of each winding and/or close to each winding (on the side opposite to the part to be tested) so as to reduce the reluctance of the magnetic circuit of each emission winding/reception winding pair, multilayer windings, for example several stacked kapton films arranged in series.

electronic components, for example amplifiers, multiplexers, demodulators, etc., located on the support, a multi-element configuration.

A multi-element configuration comprises several elements arranged on a single substrate, for example a module associated with a mechanical displacement on an axis or a matrix arrangement to prevent any mechanical displacement. Such a configuration can limit the time necessary to inspect part surfaces. The size of an element composed of at least two windings, designed particularly for detection of small defects, is often larger than the maximum pitch p required between two elements, the pitch p being determined such that, regardless of the position of a defect in a part, at least one element can detect its presence.

A first solution to increase the density of elements to achieve the pitch p consists of arranging the elements staggered in several rows, all at the same height, on the same support. Thus, if the element is twice as wide as the required pitch p, two rows of elements will be used, the elements on a single row being at a spacing of 2p. Such a configuration creates problems in interpreting data, to the extent that there is no spatial consistency in the different rows, so that it becomes essential to use a post-processing step before analysing maps (translation of rows).

Figure 5A:
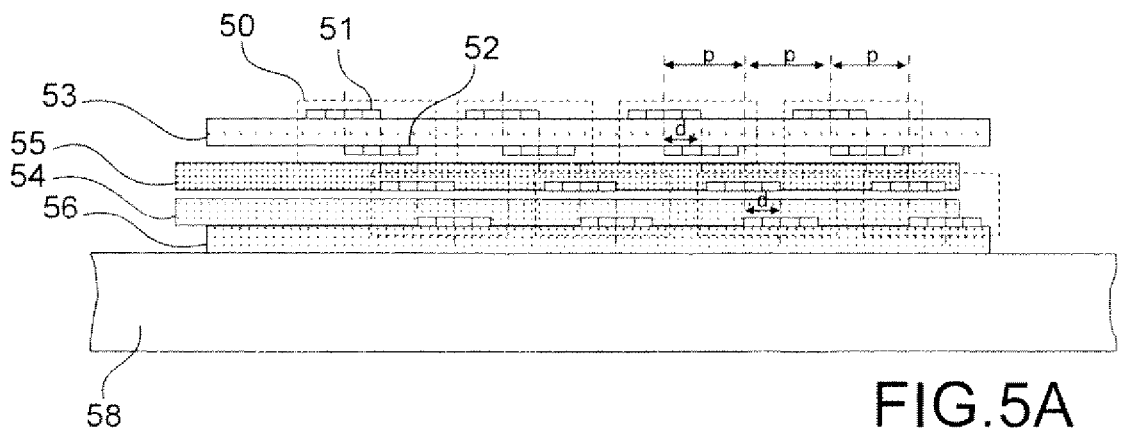
FIGS. 5A and 5B show a multi-element configuration of the device according to the invention.

A second solution shown in FIG. 5A consists of stacking the rows of elements 50 comprising an emission winding 51 and a reception winding 52, always staggered, by placing at least two substrates 53 and 54 one above the other (for example flexible kapton films) with intermediate insulations 55 and 56, each row being offset from the next row by a pitch p. By using "classical" elements, i.e. for which the distance d between the emission winding 51 and the reception winding 52 is not optimised, the induced electromotive force $V_R$ at the terminals of the reception windings is different depending on the layer to which the element belongs. This makes the step to balance the eddy current instrument difficult, particularly for multiplexed elements.

Figure 5B:
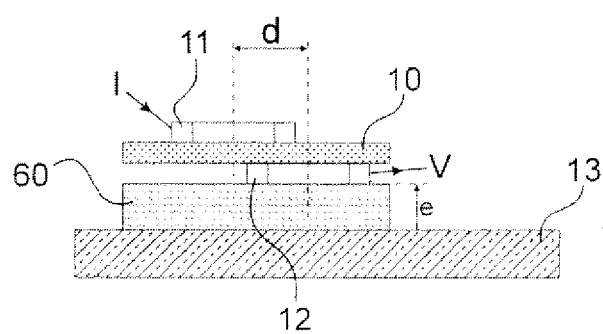

In FIG. 5B, that more particularly illustrates an element, the same references are used as in FIG. 1, with added insulation 60.

Optimisation of the distance between the emission winding and the reception winding according to the invention results in elements in which the value of the induced electromotive force $V_R$ is the same, regardless of the distance between the part 58 and the element. Therefore, this configuration is adapted more particularly to the method of optimising the distance according to the invention.

The invention claimed is:

1. Method with separate emission/reception functions for making eddy current tests on an electrically conducting part (13) with an electrical conductivity $\sigma_1$ and relative magnetic permeability $\mu_{r1}$, in which a sensor comprising at least one assembly formed from at least one emission winding (11) emitting an electromagnetic field and at least one reception winding (12) influenced by the electromagnetic fields produced by eddy currents induced in this part (13), moves above this part, characterised in that it comprises the following steps:

obtain a first complex voltage curve (20) at the terminals of a reception winding (12), depending on the distance between the corresponding emission winding (11) and this reception winding, for the nominal distance between the sensor and a portion of this part without any defects or another part without any defects, obtain at least one second complex voltage curve (21,22) at the terminals of a reception winding, as a function of the distance between the corresponding emission winding and this reception winding, for at least one distance (e) different from the nominal distance between the sensor and a portion of this part with no defects or another part without any defects, determine at least one given distance (di) that minimises the modulus of the difference between the first curve (20) and the at least one second curve (21, 22), calculate the arithmetic mean (d) of the at least one given distance (di), choose this arithmetic mean+/−20% as the distance between the two emission and reception windings detect if one or several defects are present in this part.

2. Method according to claim 1, in which the electrical conductivity $\sigma_2$ in the portion of the part with no defects or in another part without any defects, is such that $0.05 \times \sigma_1 \leq \sigma_2 \leq 20 \times \sigma_1$ and the relative magnetic permeability $\mu_{r2}$ is such that $0.05 \times \mu_{r1} \leq \mu_{r2} \leq 20 \times \mu_{r1}$.

3. Method according to claim 1, in which the step to obtain at least two curves is done by measurement or calculation.

4. Method according to claim 1, in which the emission and reception windings are arranged on each side of a support.

5. Method according to claim 4, in which the support is a flexible support in which the emission and reception windings are etched.

6. Method according to claim 5, in which the flexible support is a kapton film.

7. Method according to claim 1, in which the range of frequencies used is between 10 Hertz and 50 Megahertz.

8. Method according to claim 1, in which a magnetic material is placed at the centre of each winding and/or close to each winding, on the side opposite the part to be tested, so as to reduce the reluctance of the magnetic circuit in each emission winding/reception winding pair.

9. Device with separate emission/reception functions for making eddy current tests on an electrically conducting part, characterised in that it comprises:

at least two rows composed of at least one element formed from at least one emission winding emitting an electromagnetic field and at least one reception winding, and in that:

each row is offset from the next row by a distance p, each winding of the same nature on a particular row being at a distance n×p from its closest neighbour, where n is the number of rows, the distance between an emission winding and a reception winding of each element in each of the rows is equal to d+/−20%, where d is the arithmetic mean of at least one distance (di) that minimises the modulus of the difference between a complex voltage curve (20) for a nominal distance between the sensor and a portion of this part without any defects or another part without any defects, and at least one complex voltage curve (21, 22) for at least one distance different from the nominal distance.

10. Device according to claim 9, in which at least two rows are at different heights.

11. Device according to claim 9, in which the emission and reception windings are arranged on each side of a support for each row.

12. Device according to claim 11, in which an electrical insulation is arranged between two consecutive rows.

* * * * *